(12) United States Patent
Benassi et al.

(10) Patent No.: US 10,617,442 B2
(45) Date of Patent: Apr. 14, 2020

(54) SCALPEL

(71) Applicant: SCALJET, Crolles (FR)

(72) Inventors: Pascal Benassi, Bernin (FR); Pierre Monod, Corenc (FR); André Vuillaume, Biviers (FR)

(73) Assignee: SCALJET, Crolles (FR)

(*) Notice: Subject to any disclaimer, the term of this patent is extended or adjusted under 35 U.S.C. 154(b) by 267 days.

(21) Appl. No.: 15/562,012

(22) PCT Filed: Mar. 15, 2016

(86) PCT No.: PCT/EP2016/055571
§ 371 (c)(1),
(2) Date: Sep. 27, 2017

(87) PCT Pub. No.: WO2016/156031
PCT Pub. Date: Oct. 6, 2016

(65) Prior Publication Data
US 2018/0085140 A1 Mar. 29, 2018

(30) Foreign Application Priority Data
Apr. 3, 2015 (FR) ..................... 15 00678

(51) Int. Cl.
A61B 17/3203 (2006.01)
A61B 17/3211 (2006.01)

(52) U.S. Cl.
CPC ...... *A61B 17/3203* (2013.01); *A61B 17/3211* (2013.01)

(58) Field of Classification Search
CPC ....... A61B 2017/320071; A61B 2017/320069; A61B 2017/320082; A61B 17/320068; A61B 17/1285; A61B 17/42; A61B 17/3201; A61B 17/3203; A61B 2018/00601
See application file for complete search history.

(56) References Cited

U.S. PATENT DOCUMENTS

| 5,179,805 A | 1/1993 | Numao et al. |
| 2009/0030439 A1* | 1/2009 | Stulen ............ A61B 17/320092 606/169 |
| 2009/0254075 A1* | 10/2009 | Paz ................... A61B 17/3203 606/28 |
| 2014/0303659 A1* | 10/2014 | Aljuri ............... A61B 17/3203 606/167 |

FOREIGN PATENT DOCUMENTS

| GB | 1 445 488 | 8/1976 |
| WO | WO 03/096871 A2 | 11/2003 |
| WO | WO 2010/148125 A1 | 12/2010 |

* cited by examiner

*Primary Examiner* — Ryan J. Severson
*Assistant Examiner* — Mohamed G Gabr
(74) *Attorney, Agent, or Firm* — Renner Kenner Greive Bobak Taylor & Weber

(57) ABSTRACT

The invention relates to a scalpel comprising a conduit (1) which is connected to a pressurised liquid source (2) and which terminates in two openings, each having a diameter of between 0.05 mm and less than 0.1 mm and being disposed such as to supply two liquid jets (8, 9) that converge at a convergence point (10).

9 Claims, 2 Drawing Sheets

Zone de coupe
10

Zone de dissection
11

Zone de pneumatisation
12

SCALPEL

The invention relates to scalpels used in surgery for cutting and dissection.

In WO/03/09687 a scalpel is described that comprises a conduit which, on the one hand, communicates, in particular at one end, with a source of pressurized liquid and which, on the other hand, terminates in two openings, each having a diameter of between 0.03 mm and less than 0.1 mm, and disposed such as to supply two liquid jets that converge at a convergence point.

The invention improves this scalpel by means of a scalpel which is more accurate and which lends itself better to dissection.

The scalpel according to the invention is of the above type, characterized in that
  the convergence point is between 20 and 40 mm away from the openings, and the spacing between the two openings is between 2 and 6 mm, and
  the liquid is at a pressure of 60 to 200 bar.

The hydric scalpel of the invention uses two hydric jets with a very small diameter, at very high pressure, and the convergence angle of which is also very small.

The small angle between the jets makes it possible (in direct contradiction with what is taught by WO 03/096 871 on page 10, lines 10, 14 and 15), on the one hand, to obtain a high-energy cutting zone with a long length of about 30 to 40 mm located between the opening of the jets and their convergence point and, on the other hand, to create a liquid/air lamellar fan after the convergence point. This lamellar fan is positioned at 90° in relation to the plane defined by the two jets before their convergence point. It is therefore perfectly defined and visible in relation to them.

This liquid/air fan with a length of approximately 20 mm, has sufficient energy to dissect tissues without cutting them and without damaging organs such as arteries, tendons, etc.

Beyond the zone of the lamellar fan the jets disperse naturally by the frictional forces in the air, but a zone of approximately 20 mm, also called the pneumatization zone, directly extending the fan, remains.

It is this zone which inflates the tissues by means of hydric absorption, dissection then being implemented without causing any damage by means of the lamellar fan, and the subsequent cut in the first zone of the tool upstream of the focal point.

A lamellar fan can only be obtained if the convergence angle of the jets is limited. This angle may not exceed 12°. Beyond this value it is practically impossible to obtain a lamellar fan, the jets destroying one another and thus losing their kinetic energy, and so making the lamellar fan unsuitable for dissection. In addition, the jets explode in the form of mist, and this creates visual pollution and makes the scalpel unsuitable for any use. The angle between the two jets is preferably between 3 and 7°.

The two parameters—a small angle and high pressure—are both necessary to be able to bring about a sufficient quantity of air located on the periphery of the jets in order to form, after the impact point of the jets, a lamellar fan equatable to a scalpel, and beyond this zone, and to retain sufficient kinetic energy to atomise the hydric/air mixture and to thus generate the so-called pneumatization zone.

High pressure is indispensable for obtaining both the lamellar fan and the pneumatization zone because it is the high speed of the jets which makes it possible to bring about the quantity of air necessary for forming the fan.

The pressure of the liquid used in the invention may vary between 60 and 200 bar, preferably between 80 and 150 bar. A pressure of lower than 60 bar is insufficient to make it possible to easily bring about the cutting/dissection combination, whereas a pressure of greater than 200 bar may pose the risk of excessively harsh cutting.

The small diameter of the jets (generally between 0.07 and 0.08 mm) and the high pressure used (preferably greater than 80 bar) provides high kinetic energy that makes it possible to cut tissues with a very low liquid throughput, and this promotes elimination by suction and improves visibility and so the accuracy of the operation. The reduced diameter of the jets makes it possible, moreover, to considerably increase the accuracy of the operation.

In surgery it is essential to reduce as far as possible the fluid throughput since excessive throughput poses problems which are more or less unresolvable with regard to the elimination of said fluid.

The diameter of the openings makes it possible to limit both the fluid throughput and the frictional forces in the air, the latter being proportional to the diameter.

This diameter is preferably between 0.07 and 0.08 mm.

The energy of jets with a diameter of less than 0.3 mm is too small to be able to generate a cutting effect, even with a very high pressure of almost 200 bar.

If the diameter of the jets is greater than or equal to 0.1 mm, the hydraulic throughput is too great and causes difficulties associated with the elimination of said liquid by suction.

The convergence of the jets is brought about such as to create a mixture of the liquid that forms the jets and of the ambient air by forming a lamellar fan of which the thickness is close to the diameter of the jets. This fan creates a pneumatization effect that allows dissection that can be adjusted based on distance.

The spacing of the two openings is preferably approximately 3 mm, ranging in particular from 2 to 6 mm. The angle between the two jets is less than 12° and, preferably, is between 3 and 7°.

The cuffing zone is thus sufficiently long to be clearly differentiated from the dissection zone by the surgeon.

The cutting effect is obtained upstream of the convergence point and the dissection effect is obtained downstream of this point.

This scalpel may be used in any type of surgery (open, laparoscopic, robot-assisted . . . ). Its cutting function may be operational from the cutaneous incision, then for the sectioning of the deeper planes (aponeuroses, muscles . . . ). Its second function makes it possible to dissect fine elements, such as the neurovascular pedicles, without damage and to tear the parenchymas.

A beam formed of two distinct converging jets is directed at the organ to be operated, these jets producing after their convergence point, by virtue of said distance that makes it possible to carry a lot of air, an extremely fine lamellar fan made up of a mixture of the jets of liquid and of the air carried by the jets.

The zone upstream of the convergence point corresponds to the cutting zone of the scalpel. The fanned zone is the one used for dissection.

The preferred liquid that forms the jets is physiological serum which may be contained in a pocket and which may be pressurized with the aid of a pump.

In order to adapt to any type of surgery, the conduit may be mounted on a handle, as is conventional in open surgery, or on a support, for laparoscopic surgery.

Finally, a preferably remote-controlled faucet is provided for blocking communication between the source and the conduit, as is a preferably remote-controlled device which makes it possible to vary the pressure of the jets.

In the attached drawings, given purely as examples:

Figure 1:
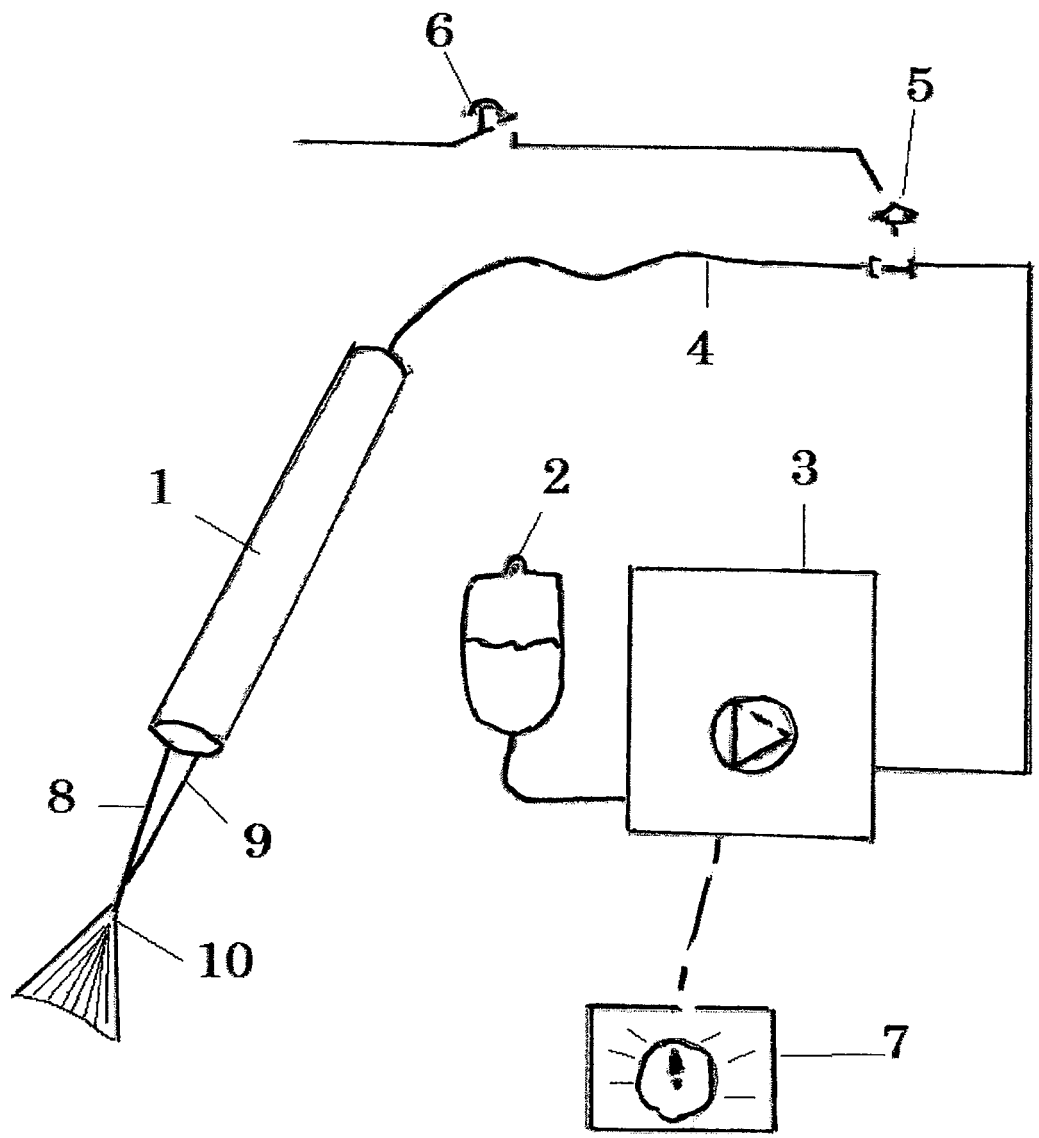
FIG. 1 shows a scalpel according to the invention.

The scalpel according to the invention comprises a tubular handle 1 that defines a conduit which communicates, by means of channeling 4, with a pocket 2 of physiological serum that is pressurized by a pump 3. Fitted to this channeling 4 is a faucet 5 with remote control 6. The pump 3 comprises a device 7 that makes it possible to vary the pressure of the physiological serum sent in the conduit of the handle 1.

This conduit opens to the outside on the end opposite to that at which the channeling 4 arrives, via two openings, each with a diameter of 0.08 mm, disposed such as to supply two jets 8, 9 that converge at a point 10.

Figure 2:
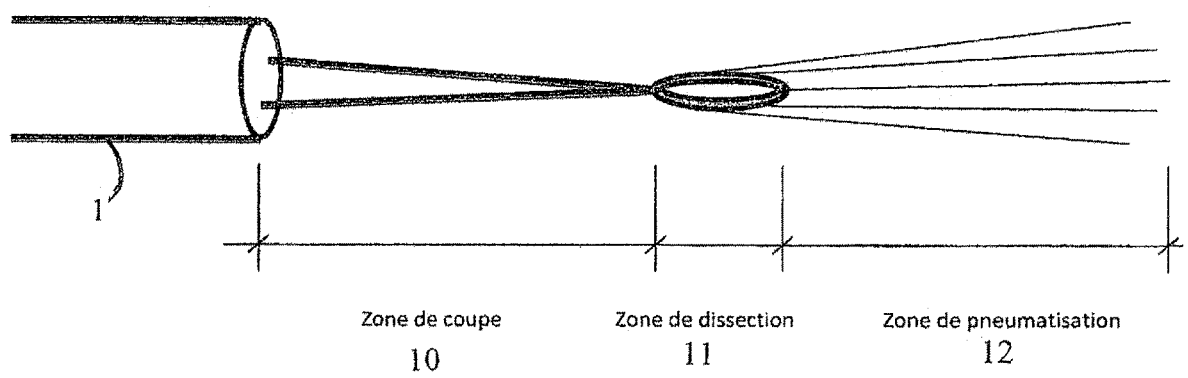
FIG. 2 is a diagram of the scalpel beam.

The beam of physiological illustrated diagrammatically in FIG. 2 comprises, from upstream to downstream, a cutting zone 10 where the two jets converge towards one another, separated from a dissection zone 11 by the convergence point. The dissection zone 11 is followed by a divergent pneumatization zone 12. The dissection zone 11 is in the form of a fan with lamellar spacing.

KEY TO THE WORDING IN THE FIGURES

FIG. 2
Zone de coupe=cutting zone
Zone de dissection=dissection zone
Zone de pneumatisation=pneumatization zone

The invention claimed is:

1. A scalpel that comprises a conduit which, on the one end, communicates with a source of pressurized liquid and which, on an opposite end, terminates in two openings, each having a diameter of between 0.03 mm and 0.1 mm, and disposed such as to supply two liquid jets that converge at a convergence point,
characterized in that
the convergence point is between 20 and 40 mm away from the openings, and the spacing between the two openings is between 2 and 6 mm, and
the liquid is at a pressure of 60 to 200 bar.

2. The scalpel according to claim 1, characterized in that the liquid is at a pressure of 80 to 150 bar.

3. The scalpel according to claim 1, characterized in that the diameter of the openings is between 0.07 and 0.08 mm.

4. The scalpel according to claim 1, characterized in that an angle between the two jets is less than 12°.

5. The scalpel according to claim 4, characterized in that the angle between the two jets is between 3 and 7°.

6. The scalpel according to claim 1, characterized in that the liquid is physiological serum.

7. The scalpel according to claim 1, characterized in that the conduit is arranged in a handle or on a support.

8. The scalpel according to claim 1, characterized by a faucet for blocking communication between the source and the conduit.

9. The scalpel according to claim 1, characterized by a device that makes it possible to vary the pressure of the jets.

* * * * *